United States Patent
Olivier-Bourbigou et al.

(10) Patent No.: US 10,662,133 B2
(45) Date of Patent: May 26, 2020

(54) PROCESS FOR THE NEUTRALIZATION OF A CATALYTIC SYSTEM FOR THE DIMERIZATION OF OLEFINS CONTAINING AT LEAST ONE HALOGENATED DERIVATIVE

(71) Applicant: IFP Energies Nouvelles, Rueil-Malmaison (FR)

(72) Inventors: Helene Olivier-Bourbigou, Saint Genis-Laval (FR); Francois Hugues, Charly (FR); Emmanuel Pellier, Tupin Semons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 11 days.

(21) Appl. No.: 15/850,622

(22) Filed: Dec. 21, 2017

(65) Prior Publication Data

US 2018/0179127 A1  Jun. 28, 2018

(30) Foreign Application Priority Data

Dec. 22, 2016 (FR) ...................................... 16 63138

(51) Int. Cl.
*C07C 7/148* (2006.01)
*C07C 2/32* (2006.01)
*C07C 7/10* (2006.01)
*C07C 2/22* (2006.01)

(52) U.S. Cl.
CPC ............ *C07C 7/14875* (2013.01); *C07C 2/22* (2013.01); *C07C 2/32* (2013.01); *C07C 7/10* (2013.01); C07C 2531/14 (2013.01); C07C 2531/22 (2013.01)

(58) Field of Classification Search
CPC ............. C07C 7/148; C07C 2/22; B01J 31/14
See application file for complete search history.

(56) References Cited

U.S. PATENT DOCUMENTS

| 4,283,305 A | * | 8/1981 | Chauvin | .............. B01J 31/0231 502/117 |
| 4,401,559 A | * | 8/1983 | Gaillard | .................... C07C 7/10 208/262.1 |

FOREIGN PATENT DOCUMENTS

FR        2504122 A1    10/1982

OTHER PUBLICATIONS

Search Report in corresponding French application No. 1663138 dated Jul. 5, 2017.

* cited by examiner

*Primary Examiner* — Youngsul Jeong
(74) *Attorney, Agent, or Firm* — Millen, White, Zelano and Branigan, P.C.

(57) ABSTRACT

The invention concerns a process for the neutralization of a catalytic system for the oligomerization of olefins, said catalytic system comprising at least one halogenated derivative, characterized in that the reaction effluent is brought into contact with at least one nitrile compound.

13 Claims, No Drawings

PROCESS FOR THE NEUTRALIZATION OF A CATALYTIC SYSTEM FOR THE DIMERIZATION OF OLEFINS CONTAINING AT LEAST ONE HALOGENATED DERIVATIVE

The present invention relates to a process for neutralizing a catalytic system for the oligomerization of olefins, in particular a process for the dimerization of olefins, said catalytic system comprising at least one halogenated derivative.

PRIOR ART

The transformation of light olefins using a homogeneous catalyst based on a transition metal, in particular based on nickel, associated with a halogenated activator, for example a chloroalkylaluminium, has been studied since the 1950s. That research has led to the development and commercialization of a variety of processes.

As an example, octenes or hexenes or nonenes are respectively produced by the dimerization of butenes or the oligomerization of propylene using the Dimersol™ process from Axens (Revue de the Institut Français du Pétrole [Review of the French Oil Institute], Vol. 37, N°5, September-October 1982, p 639). The octenes can be transformed in good yields by the hydroformylation reaction followed by hydrogenation into isononanols. These C9 alcohols (i.e. containing 9 carbon atoms) are in particular used for the synthesis of phthalate type plasticizers for PVC. The hexenes or the nonenes may also be used as a base for a fuel with a very good octane number.

Developing catalytic systems which are capable of dimerizing olefins involves selecting the transition metal and suitable ligands. Of the existing systems of catalysts, a number of catalytic systems based on nickel using various ligands have been developed. Examples which may in particular be mentioned are complexes of halides of π-allyl nickel phosphine with Lewis acids, as described in the French patent FR 1 410 430 B, complexes of nickel phosphine halides with Lewis acids as described in the patent U.S. Pat. No. 3,485,881 A, complexes of nickel with iminoimidazole ligands as described in the French patent FR 2 979 836 B and carboxylates of nickel with hydrocarbylaluminium halides, as described in the patent U.S. Pat. No. 3,321,546 A. In such processes, it turns out to be necessary to neutralize the catalyst at the end of the reaction to prevent the reaction continuing in an unwanted manner.

Patent FR 2 114 114 B describes a process for deactivating a catalyst for the dimerization of olefins, containing at least one halogenated compound involving contact of the reaction effluent with anhydrous ammonia or an amine.

The patent U.S. Pat. No. 4,642,408 B describes a process for the treatment of an effluent from an olefins oligomerization reaction in the presence of a catalyst containing a halogenated compound by treatment of the effluent in a first step (1) with a solution of anhydrous ammonia, then in a second step (2) by washing with an aqueous solution of alkali metals, with the condition that the effluent is treated before or after steps (1) and (2) using oxygen or a gas containing oxygen.

The processes described in the prior art are satisfactory as regards the neutralization efficiency, but cause problems as regards safety which are linked to the use of certain inhibitors such as ammonia or amines, in particular because they are physically in the gaseous state and/or because of their toxicity.

The Applicant's research has led to the development of a novel process for neutralizing a catalytic system for the oligomerization of olefins, preferably for the dimerization of olefins, said catalytic system comprising at least one halogenated derivative, employing a step for contact of the reaction effluent with at least one nitrile compound.

It has surprisingly been shown that such a process can be used to effectively neutralize a catalytic system comprising at least one halogenated derivative used in the olefins oligomerization reaction. In particular, the process in accordance with the invention can be used to prevent the formation of chlorine-containing organic products obtained from secondary reactions between the halogenated derivatives present in the catalytic system and the olefins formed during the dimerization reaction.

One aim of the neutralization process in accordance with the invention is to prevent the olefins formed from becoming contaminated by non-negligible quantities of halogens originating from the catalytic system, in particular by the formation of halogenated organic products (chlorine-containing or bromine-containing). These halogens may be particularly harmful and difficult to eliminate from the olefins, in particular in the case in which the olefins are subsequently used in specific reactions such as the hydroformylation reaction or hydrogenation reaction.

DETAILED DESCRIPTION OF THE INVENTION

The invention concerns a process for neutralizing a catalytic system for the oligomerization of olefins, preferably for the dimerization of olefins, said catalytic system comprising at least one halogenated derivative, characterized in that the reaction effluent comprising said catalytic system is brought into contact with at least one nitrile compound RC≡N comprising at least one carbonitrile compound —C≡N, R being a hydrocarbyl group containing 1 to 20 carbon atoms, which may be saturated or unsaturated, linear or branched, cyclic or aromatic, which may or may not comprise a heteroatom.

The process in accordance with the invention is applicable to reaction effluents comprising dimers and oligomers produced by reactions for the dimerization or oligomerization of olefins, employing a catalytic system comprising a halogenated derivative. Advantageously, said catalytic system is a homogeneous catalytic system in the liquid phase.

Oligomerization is defined as the transformation of a monomer unit $C_nH_{2n}$ (n=2 to 10) into a compound or a mixture of compounds with general formula $C_pH_{2p}$ in which $4 \leq p \leq 80$, preferably in which $4 \leq p \leq 50$, more preferably in which $4 \leq p \leq 26$ and yet more preferably in which $4 \leq p \leq 14$.

The reaction effluent is advantageously obtained from an oligomerization process, preferably from a process for the dimerization of olefins operated at a total pressure in the range from atmospheric pressure to 20 MPa, preferably in the range 0.5 to 8 MPa, and at a temperature in the range −40° C. to +250° C., preferably in the range −20° C. to 150° C.

The olefins used as a feed in the process for the oligomerization of olefins, or preferably in the process for the dimerization of olefins, are olefins containing 2 to 10 carbon atoms, and preferably said olefins are selected from ethylene, propylene, n-butenes and n-pentenes, alone or as a mixture, pure or diluted; preferably, the olefins used are n-butenes, propylene and/or ethylene. In the case in which said olefins are diluted, said olefins are diluted with one or more alkane(s) such as those found in "cuts" obtained from oil refining processes, such as catalytic cracking or steam cracking. Said olefins may derive from non-fossil sources such as biomass. As an example, the olefins used in the oligomerization process may advantageously be produced from alcohols, and in particular by the dehydration of alcohols.

The process for the oligomerization of olefins, preferably the process for the dimerization of olefins, may be operated in the presence of a solvent. In such a case, the solvent may be selected from organic solvents and from saturated, unsaturated, aromatic or non-aromatic hydrocarbons, cyclic or otherwise. In particular, said solvent may be selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, pure or as a mixture, and ionic liquids.

The neutralization process in accordance with the invention is applicable to any catalytic system for the oligomerization or the dimerization of olefins employing a catalyst comprising a halogenated derivative. In accordance with the process of the invention, the catalytic system, which is preferably homogeneous, comprises at least one halogenated derivative.

The halogenated derivative may be any halogenated compound which is known to the person skilled in the art in catalytic systems for the oligomerization of olefins.

Advantageously, the halogenated derivative is an alkyl aluminium halide with formula $AlR'_m X_{3-m}$ in which R' is a hydrocarbyl radical containing 1 to 12 carbon atoms, such as an alkyl, an aryl, an aralkyl, an alkaryl or a cycloalkyl, X is an atom of chlorine or bromine, X preferably being an atom of chlorine, and m is a number in a range of from greater than 0 to 2.

Preferably, the halogenated derivative is selected from ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), and diethylaluminium chloride ($Et_2AlCl$), used alone or as a mixture.

In some catalytic systems, the alkyl aluminium halides may optionally be enriched in aluminium trihalide with formula $AlX_3$. Non-limiting examples which may be cited are as follows: dichloroethylaluminium enriched with aluminium trichloride and having the formula $AlEt_{0.9}Cl_{2.1}$, for example, dichloroisobutylaluminium enriched with aluminium trichloride and having the formula $AlisBu_{0.9}Cl_{2.1}$, for example.

In a variation of the process, the catalytic system may be used in a two-phase liquid-liquid medium containing a medium with an ionic nature which is not or is only slightly miscible with the organic phase containing the products. A catalytic system of this type is described in the patent U.S. Pat. No. 5,104,840 B. In such a case, the medium with an ionic nature may comprise at least one salt with the formula $Q^+A^-$, in which $Q^+$ is a quaternary ammonium or phosphonium cation or a mixture of the two or a lithium cation, and $A^-$ is a coordinating or non-coordinating anion, preferably selected from the group formed by halogenoaluminates, organohalogenoaluminates, organogallates, organohalogenogallates or a mixture of at least two of these compounds.

In addition to the halogenated derivative, the catalytic system advantageously comprises a precursor of nickel.

The precursor of nickel may be selected from nickel(II) chloride, nickel(II)(dimethoxyethane) chloride, nickel(II) bromide, nickel(II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate for example, nickel (II) octoate, nickel(II) phenates, nickel(II) acetate, nickel(II) trifluoroacetate, nickel(II) triflate, nickel(II) acetylacetonate, nickel(II) hexafluoroacetylacetonate, allylnickel(II) chloride, allylnickel(II) bromide, methallylnickel(II) chloride dimer, allylnickel(II) hexafluorophosphate, methallylnickel (II) hexafluorophosphate, nickel(II) biscyclopentadienyl, nickel(II) bisallyl and nickel(II) bismethallyl, in their hydrated form or non-hydrated form, used alone or as a mixture. Said nickel precursors may optionally be complexed with Lewis bases.

At the outlet from the process for the oligomerization of olefins, preferably the process for the dimerization of olefins, the reaction effluent may comprise unconverted olefins, alpha-olefins such as 1-butene, 1-hexene, 1-octene, and other C4 to C10 reaction products, as well as any reaction solvent. Said effluent also comprises at least a portion of the catalytic system used in the reaction.

Advantageously, in accordance with the invention, the effluent from the reaction for the oligomerization of olefins, preferably from the reaction for the dimerization of olefins, is brought into contact with a nitrile compound RC≡N comprising at least one carbonitrile group —C≡N, R being a hydrocarbyl group containing 1 to 20 carbon atoms, which may be saturated or unsaturated, linear or branched, cyclic or aromatic, which may or may not comprise a heteroatom. Preferably, the hydrocarbyl group R contains 1 to 15 carbon atoms, more preferably 1 to 10 carbon atoms. The heteroatom is selected from sulphur, oxygen, nitrogen and phosphorus.

The contact between the reaction effluent—comprising the catalytic system comprising a halogenated derivative—and the nitrile compound may be carried out directly at the outlet from the olefin oligomerization reaction. When the oligomerization is carried out in a two-phase liquid-liquid medium containing a medium with an ionic nature, the organic phase containing the oligomers is preferably separated from the ionic liquid phase by decanting before bringing the reaction effluent into contact with the nitrile compound.

Preferably, the nitrile compound is selected from acetonitrile, propionitrile, butanenitrile or butyronitrile, hexanenitrile, cyclohexanenitrile, acrylonitrile, benzonitrile and cyclopentanecarbonitrile. More preferably, the nitrile compound is selected from acetonitrile, propionitrile, butyronitrile. Yet more preferably, the nitrile compound is acetonitrile.

A quantity of nitrile compound which is sufficient to substantially eliminate all of the halogen from the catalytic system is employed in the neutralization process of the invention. Preferably, the molar ratio between the nitrile compound and the halogenated derivative is in the range 1 to 30, preferably in the range 1 to 15, and more preferably in the range 1 to 10.

Advantageously, the contact between the effluent from the olefins oligomerization reaction, preferably from the olefins dimerization reaction, and the nitrile compound is carried out at a temperature in the range −20° C. to 100° C. Advantageously, the neutralization temperature is that at which the olefins oligomerization reaction, in particular the olefins dimerization reaction, has been carried out.

The effluent which has thus been neutralized by the neutralization process in accordance with the invention could optionally then be treated with sodium hydroxide or with water or with acid, and then undergo a fractionation.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1663138, filed Dec. 22, 2016 are incorporated by reference herein.

EXAMPLES

The examples below illustrate the invention without limiting its scope.

Example 1

Effluent without Treatment with a Nitrile Compound (Not in Accordance with the Invention)

100 mL of a cut of octenes obtained from the dimerization of butenes (termed a dimate) was introduced into a drum purged with dry nitrogen. Next, 0.043% by weight (with respect to the dimate) of nickel(II) octoate followed by 0.18% by weight (with respect to the dimate) of ethylaluminium dichloride (EtAlCl$_2$=EADC) were introduced. The catalytic system had a molar ratio Al/Ni=15 and comprised 1000 ppm of chlorine introduced via the EADC. This orange coloured solution was heated for 5 minutes at 50° C., with stirring (2000 rpm).

50 mL of aqueous 20% sodium hydroxide which had been heated to 50° C. was introduced into this solution using a syringe, and with stirring. Stirring was maintained for 5 minutes then halted. The organic and aqueous phases were decanted, then the aqueous phase was extracted with a cannula. 50 mL of water, preheated to 50° C., was added to the organic phase. It was all stirred for 5 minutes (2000 rpm). The phases settled out instantaneously. They were clear and colourless. Two other water washes were carried out. The aqueous phases were removed. The organic phase (dimate) was analysed by gas phase chromatography (GC) and by X ray fluorescence (XRF) in order to analyse the chlorine.

Example 2

Effluent with Treatment Using an Acetonitrile in an Acetonitrile/EADC Molar Ratio of 2.5 (in Accordance with the Invention)

100 mL of a cut of octenes obtained from the dimerization of butenes (termed a dimate) was introduced into a drum purged with dry nitrogen. Next, 0.043% by weight (with respect to the dimate) of nickel(II) octoate followed by 0.18% by weight (with respect to the dimate) of ethylaluminium dichloride (EtAlCl$_2$=EADC) were introduced. The catalytic system had a molar ratio Al/Ni=15 and comprised 1000 ppm of chlorine introduced via the EADC. This orange coloured solution was heated for 5 minutes at 50° C., with stirring (2000 rpm).

Acetonitrile (CH$_3$CN) with the trade mark LiPerSolv Chromanorm sold by VWR containing 30 ppm of H$_2$O (commercial analytical grade, 99.9%) was then injected using a syringe, in an acetonitrile/EADC molar ratio of 2.5. It was stirred for 5 minutes. A whitish precipitate was formed. Then sodium hydroxide was introduced, as before. The precipitate disappeared when the sodium hydroxide was introduced. The procedure was then identical to that described in Example 1 with two washes with water. The phases settled out instantaneously.

Example 3

Effluent with Treatment Using an Acetonitrile in an Acetonitrile/EADC Molar Ratio of 5 (in Accordance with the Invention)

This example was carried out as described for Example 2, with the exception that the acetonitrile/EADC molar ratio was 5.

Example 4

Effluent with Treatment Using an Acetonitrile in an Acetonitrile/EADC Molar Ratio of 5 (in Accordance with the Invention)

This example was carried out as described for Example 3, with the exception that an acetonitrile CH$_3$CN with the trade mark PanReac sold by Grosseron containing 0.1% by weight of H$_2$O (commercial analytical grade, 99.7%) was used.

Example 5

Effluent with Treatment Using an Acetonitrile in an Acetonitrile/EADC Molar Ratio of 10 (in Accordance with the Invention)

This example was carried out as described for Example 4, with the exception that the acetonitrile/EADC molar ratio was 10.

Table 1 reports the results obtained from the GC and XRF analyses of the effluents without treatment (Example 1) and of the effluents treated using the neutralization process in accordance with the invention.

TABLE 1

| | | Analysis of effluents | | | | | |
|---|---|---|---|---|---|---|---|
| | | | | | | XRF analysis of chlorine | |
| CH$_3$CN | | | GC analysis of dimate (% by weight) | | | | +/−* |
| Dimate/EADC | CH$_3$CN/EADC | % C4 | % C6 | % C8 | % C10+ | ppm Cl | ppm Cl |
| Initial dimate | | 0.097 | 2.255 | 97.3 | 0.343 | <5 | |

TABLE 1-continued

Analysis of effluents

| CH₃CN | | GC analysis of dimate (% by weight) | | | | XRF analysis of chlorine | |
|---|---|---|---|---|---|---|---|
| Dimate/EADC | CH₃CN/EADC | % C4 | % C6 | % C8 | % C10+ | ppm Cl | +/−* ppm Cl |
| Example 1 (not in accordance) | — | 0.06 | 2.103 | 95.15 | 2.693 | 313 | 8 |
| Example 2 (CH₃CN grade 1) | 2.5 | 0.076 | 2.091 | 97.45 | 0.385 | 9 | 2 |
| Example 3 (CH₃CN grade 1) | 5 | 0.059 | 1.941 | 97.52 | 0.478 | 7 | 2 |
| Example 4 (CH₃CN grade 2) | 5 | 0.078 | 2.115 | 97.46 | 0.345 | 7 | 2 |
| Example 5 (CH₃CN grade 2) | 10 | 0.074 | 2.079 | 97.45 | 0.394 | 7 | 2 |

*uncertainty in the measurement

The quantity of chlorine after treatment using the acetonitrile neutralization process in accordance with the invention was much smaller than that obtained without treatment.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process comprising neutralization of a catalytic system from oligomerization of olefins, said catalytic system comprising at least one halogenated derivative that is an alkyl aluminium halide with formula AlR'$_m$X$_{3-m}$ in which R' is a hydrocarbyl radical containing 1 to 12 carbon atoms, X is an atom of chlorine or bromine, and m is a number in a range of from greater than 0 to 2, by contacting a reaction effluent from the oligomerization of olefins comprising said catalytic system with at least one nitrile compound RC≡N comprising at least one carbonitrile compound —C≡N, R being a hydrocarbyl group containing 1 to 20 carbon atoms, which is saturated or unsaturated, linear or branched, cyclic or aromatic, and optionally comprises a heteroatom, at a molar ratio between the nitrile compound and the halogenated derivative (nitrile compound/halogenated derivative) of 1 to 30, whereby the catalytic system is neutralized due to said contacting, and obtaining a neutralized effluent.

2. The process as claimed in claim 1, in which the hydrocarbyl group R contains 1 to 15 carbon atoms.

3. The process as claimed in claim 1, in which the nitrile compound is acetonitrile, propionitrile, butanenitrile, butyronitrile, hexanenitrile, cyclohexanenitrile, acrylonitrile, benzonitrile, or cyclopentanecarbonitrile.

4. The process as claimed in claim 1, comprising contacting the reaction effluent from the oligomerization of olefins with the at least one nitrile compound is carried out at a temperature of −20° C. to 100° C.

5. The process as claimed in claim 1, in which the oligomerization of olefins is a process for dimerization of olefins.

6. The process as claimed in claim 1, in which the halogenated derivative is ethylaluminium sesquichloride (Et$_3$Al$_2$Cl$_3$), methylaluminium dichloride (MeAlCl$_2$), ethylaluminium dichloride (EtAlCl$_2$), isobutylaluminium dichloride (iBuAlCl$_2$), or diethylaluminium chloride (Et$_2$AlCl), used alone or as a mixture.

7. The process as claimed in claim 1, in which olefins used in the oligomerization of olefins are olefins containing 2 to 10 carbon atoms.

8. The process as claimed in claim 1, comprising contacting the reaction effluent from the oligomerization of olefins with the at least one nitrile compound at a molar ratio between the nitrile compound and the halogenated derivative (nitrile compound/halogenated derivative) of 1 to 15.

9. The process as claimed in claim 1, comprising contacting the reaction effluent from the oligomerization of olefins with the at least one nitrile compound at a molar ratio between the nitrile compound and the halogenated derivative (nitrile compound/halogenated derivative) of 1 to 10.

10. The process as claimed in claim 1, comprising contacting the reaction effluent from the oligomerization of olefins with the at least one nitrile compound at a molar ratio between the nitrile compound and the halogenated derivative (nitrile compound/halogenated derivative) of 1 to 5.

11. The process as claimed in claim 1, comprising contacting the reaction effluent from the oligomerization of olefins with the at least one nitrile compound at a molar ratio between the nitrile compound and the halogenated derivative (nitrile compound/halogenated derivative) of 1 to 2.5.

12. The process according to claim 1, further comprising treating the neutralized effluent with water, sodium hydroxide, or acid, followed by fractionation.

13. A process consisting of neutralization of a catalytic system from oligomerization of olefins, said catalytic system comprising at least one halogenated derivative that is an alkyl aluminium halide with formula AlR'$_m$X$_{3-m}$ in which R' is a hydrocarbyl radical containing 1 to 12 carbon atoms, X is an atom of chlorine or bromine, and m is a number in a range of from greater than 0 to 2, by contacting a reaction effluent from the oligomerization of olefins comprising said catalytic system with at least one nitrile compound RC≡N comprising at least one carbonitrile compound —C≡N, R being a hydrocarbyl group containing 1 to 20 carbon atoms, which is saturated or unsaturated, linear or branched, cyclic or aromatic, and optionally comprises a heteroatom, at a molar ratio between the nitrile compound and the halogenated derivative (nitrile compound/halogenated derivative)

of 1 to 30, whereby the catalytic system is neutralized due to said contacting, and obtaining a neutralized effluent.

* * * * *